United States Patent [19]

Montgomery et al.

[11] Patent Number: 5,128,458
[45] Date of Patent: Jul. 7, 1992

[54] 2',3'-DIDEOXY-4'-THIORIBONUCLEOSIDES AS ANTIVIRAL AGENTS

[75] Inventors: John A. Montgomery; John A. Secrist, III, both of Birmingham, Ala.

[73] Assignee: Southern Research Institute, Birmingham, Ala.

[21] Appl. No.: 639,021

[22] Filed: Jan. 9, 1991

Related U.S. Application Data

[63] Continuation-in-part of Ser. No. 513,270, Apr. 20, 1990, abandoned.

[51] Int. Cl.$^5$ .................. C07H 19/00; C07F 11/00
[52] U.S. Cl. .................. 536/4.1; 544/264; 536/24; 536/26; 536/23
[58] Field of Search .................. 536/4.1, 23, 24, 26

[56] References Cited

PUBLICATIONS

Reist, et al, J. Am. Chem. Soc., 86, 5658 (1964).
Miura, et al., Purine and Pyrimidine Metabolism in Man, V, Part B, (Plenum Publishing Corp., 1986) p. 667.
Richie, et al., Can. J. Chem., 56, 794 (1977).
Reist, et al., J. Org. Chem., 33, 189 (1968).
Ototani, et al., J. Med. Chem., 17, 535 (1974).
Fu, et al., J. Org. Chem., 41, 3831 (1976).
Whistler et al., J. Org. Chem., 35, 519 (1970).

Primary Examiner—Johnnie R. Brown
Assistant Examiner—L. Eric Crane
Attorney, Agent, or Firm—Roylance, Abrams, Berdo & Goodman

[57] ABSTRACT

2'3'-dideoxy-4'-thioribonucleosides useful as antiviral agents in the treatment and prevention of AIDS are disclosed. In accordance with one aspect of the invention there are provided compounds of the formula

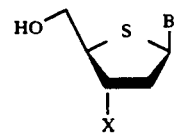

where X=H, $N_3$ or F, and B is a member selected from the group consisting of pyrimidine, 5-azapyrimidine, 6-azapyrimidine, 3-deazapyrimidine, purine, 3-deazapurine, 7-deazapurine, 8-azapurine, and 2-azapurine bases.

The intermediate 1-O-acetyl-5-O-t-butyldiphenylsilyl-4-thio-2,3-dideoxyribofuranose useful in the production of certain of the 2',3'-dideoxy-4'-thioribonucleosides is also disclosed.

8 Claims, No Drawings

2',3'-DIDEOXY-4'-THIORIBONUCLEOSIDES AS ANTIVIRAL AGENTS

CROSS-REFERENCE TO RELATED APPLICATION

This application is a continuation-in-part of co-pending application No. 07/513,270, filed Apr. 20, 1990, now abandoned.

BACKGROUND OF THE INVENTION

1. Field of the Invention

This invention relates to 2',3'-dideoxy-4'-thioribonucleosides and to their use as antiviral, especially anti-AIDS agents.

2. Description of the Related Art

2',3'-Dideoxynucleosides are known to be potent and selective agents for the treatment of AIDS. Within this series of compounds, dideoxycytidine, dideoxyinosine and AZT (3'-azido-3'-deoxythymidine) have been found to be particularly potent. However, each of these compounds produce undesirable side effects.

Thionucleoside analogues of 2',3'-dideoxynucleosides and their use as antiviral agents have not been previously reported.

Several 4'-thionucleosides have been reported in the literature. Reist, et al, *J. Am. Chem. Soc.*, 86, 5658 (1964) disclose L and D forms of 4'-thioriboadenosine. Biological effects of 4'-thioriboadenosine are described in Miura, et al in *Purine and Pyrimidine Metabolism in Man, V, Part B*, (Plenum Publishing Corp., 1986) p. 667. Richie, et al, *Can. J. Chem.*, 56, 794 (1977) disclose the synthesis of 9-(3-deoxy-4-thio-β-D-erythro-pentofuranosyl)adenine (4'-thiocordycepin). Reist, et al, *J. Org. Chem.*, 33, 189 (1968) describe the synthesis of adenine nucleosides of 4-thio-D-xylose and 4-thio-D-arabinose. Ototani, et al. *J. Med. Chem.*, 17, 535 (1974) disclose the preparation and antitumor activity of 4'-thio-1-β-D-arabinofuranosylcytosine and 2,2'-anhydro-4'-thio-1-β-D-arabinofuranosylcytosine hydrochloride.

Fu, et al, *J. Org. Chem.*, 41, 3831 (1976) disclose a method for the preparation of anomeric methyl-2-deoxy-4-thio-D-erythro-pentofuranosides and suggest that the furanosides could be used as precursors for the synthesis of 2'-deoxy-4'-thionucleosides.

SUMMARY OF THE INVENTION

It has now been found that certain 2',3'-dideoxy-4'thioribonucleosides have useful antiviral activities. Further, these compounds show reduced cytotoxicity in comparison to dideoxycytidine and AZT. Thus, in accordance with this invention, there are provided novel compounds represented by the formula

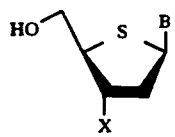

wherein:
X=H, N$_3$, or F, and
B is a nitrogenous heterocyclic base selected from the group consisting of pyrimidine, 5-azapyrimidine, 6-azapyrimidine, 3-deazapyrimidine, purine, 3-deazapurine, 7-deazapurine, 8-azapurine, and 2-azapurine bases. By the term "pyrimidine base" is meant any pyrimidine derivative including, but not limited to, uracil (2,4-dioxopyrimidine), thymine (5-methyl-2,4-dioxopyrimidine), cytosine (4-amino-2oxopyrimidine), and 5-methylcytosine (4-amino-5-methyl-2oxopyrimidine), and derivatives having an alkyl or trifluoromethyl group or a halogen attached to the $C^5$ heterocyclic carbon. By the term "5-azapyrimidine base" is meant any 5-azapyrimidine derivative including, but not limited to, 5-aza-2,4-dioxopyrimidine and 4-amino-5-aza-2-oxopyrimidine. By the term "6-azapyrimidine base" is meant any 6-azapyrimidine derivative including, but not limited to, 6-aza-2,4-dioxopyrimidine, 4-amino-6-aza-2-oxopyrimidine, and derivatives having a methyl group or halogen attached to the $C^5$ heterocyclic carbon. By the term "3-deazapyrimidine base" is meant any 3-deazapyrimidine derivative including, but not limited to, 3-deaza-2,4-dioxopyrimidine, 4-amino-3-deaza-2-oxopyrimidine, and derivatives having a methyl group or halogen attached to the $C^5$ heterocyclic carbon. By the term "purine base" is meant any purine derivative including, but not limited to, adenine (6-aminopurine), guanine (2-amino-6-oxopurine), hypoxanthine, 2-aminopurine, 2,6-diaminopurine, 2-chloro-6-aminopurine, 6-chloroaminopurine, and N$^6$-methyladenine, and derivatives having a halogen attached to the $C^2$ heterocyclic carbon. By the term "3-deazapurine base" is meant any 3-deazapurine derivative including, but not limited to, 6-amino-3-deazapurine, 3-deaza-6-oxopurine, and derivatives having an amino group or halogen attached to the $C^2$ heterocyclic carbon. By the term "7-deazapurine base" is meant any 7-deazapurine derivative including, but not limited to, 6-amino-7-deazapurine, 7-deaza-6-oxopurine, and derivatives having an amino group or a halogen attached to the $C^2$ heterocyclic carbon. By the term "8-azapurine base" is meant any 8-azapurine derivative including, but not limited to, 6-amino-8-azapurine, 8-aza-6-oxopurine, and derivatives having a halogen attached to the $C^2$ heterocyclic carbon. By the term "2-azapurine base" is meant any 2-azapurine derivative including, but not limited to, 6-amino-2-azapurine and 2-aza-6-oxopurine.

According to another aspect of this invention, there is administered to a human infected with the human immunodeficiency virus a therapeutically effective amount of a compound represented by the formula

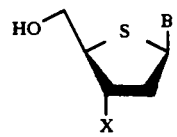

wherein:
X=H, N$^3$, or F, and
B is a nitrogenous heterocyclic base selected from the group consisting of pyrimidine, 5-azapyrimidine, 6-azapyrimidine, 3-deazapyrimidine, purine, 3-deazapurine, 7-deazapurine, 8-azapurine, and 2-azapurine bases.

In accordance with still another aspect of this invention, there is provided a novel intermediate useful in the preparation of 2',3'-dideoxy-4'-thioribonucleosides.

DETAILED DESCRIPTION OF THE INVENTION

The compounds of this invention are prepared by coupling the appropriate sugar with purine and pyrimidine bases or with purine and pyrimidine analogues such as 5-azapyrimidines, 6-azapyrimidines, 3-deazapyrimidines, 3-deazapurines, 7-deazapurines, 8-azapurines, and 2-azapurines. Some synthetic transformations have been carried out by normal literature methods. Deprotection has been carried out by standard methodology. The specific procedure for certain compounds are presented in the examples which follow.

The preparation of 1-(2-deoxy-3-azido-4-thio-β-D-ribofuranosyl)thymine begins with 1-(2-deoxy-4-thio-β-D-ribofuranosyl)thymine (Formula 1)

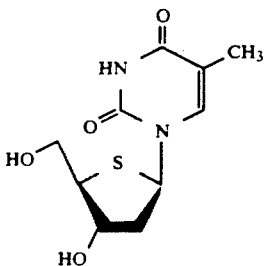

The preparation of 1 is described in U.S. application Ser. No. 07/408,040, filed Sep. 15, 1989, now abandoned, by the same inventors and commonly assigned to Southern Research Institute, the disclosure of which is hereby incorporated by reference.

The preparation may be illustrated by the following reaction scheme, the details of which are provided in Examples 1-4 below.

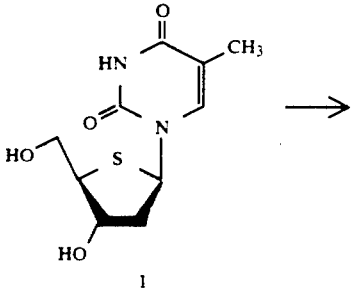

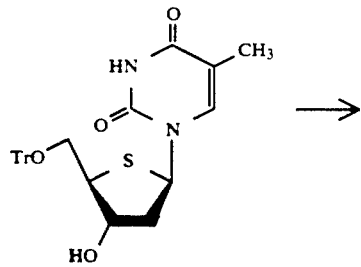

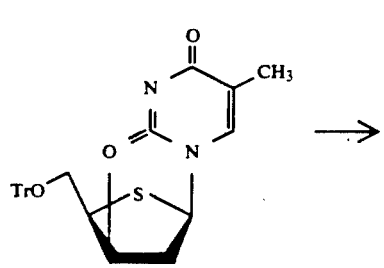

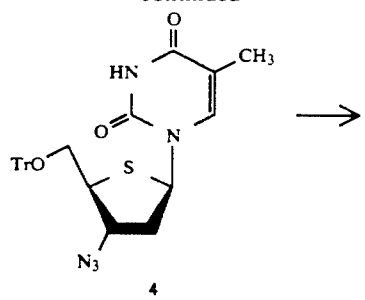

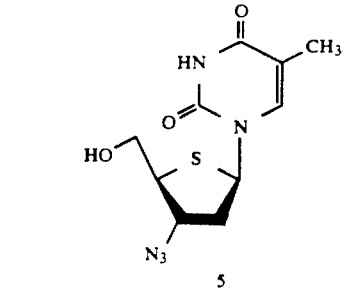

The preparation of 2',3'-dideoxy-4'-thioribonucleosides begins with (S)-O-t-butyldiphenylsilyl-5-hydroxymethyl-1,4-butyrolactone (Compound 6).

The preparation of 6 is described in S. Hanessian and P. J. Murray, *Tetrahedron*, 1987, 43, 5055–5072, the disclosure of which is incorporated herein by reference. The preparation of the intermediate, 1-O-acetyl-5-O-t-butyldiphenylsilyl-4-thio-2,3,dideoxytibofuranose (Compound 10)

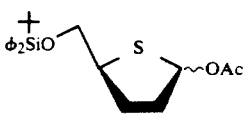

is illustrated by the following reaction scheme, the details of which are provided in Examples 5-8.

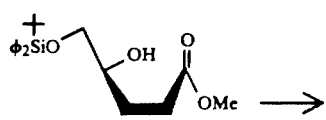

-continued

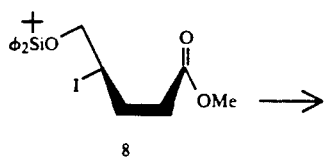
8

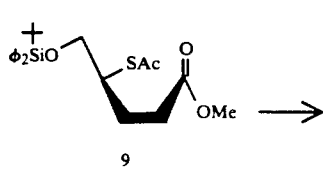
9

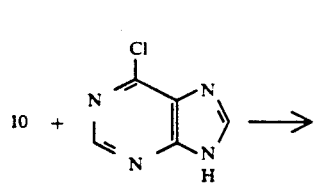
10

Compound 10 can be reacted with various purines, pyrimidines 3-deazapurines, 7-deazapurines, 8-azapurines, 2-azapurines, 5-azapyrimidines, 6-azapyrimidines, and 3-deazapyrimidines to give anomeric 5'-O-t-butyldiphenylsilyl-protected 4'-thio-2',3'-dideoxyribonucleosides such as compounds 11 through 14 and compound 26 as illustrated in the following reactions schemes and described in Examples 9–12, 24 and 26.

10 + 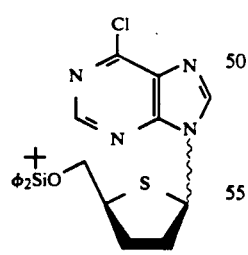 →

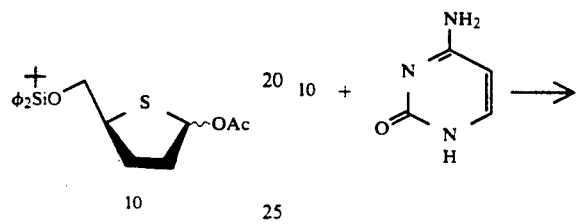
11

10 + 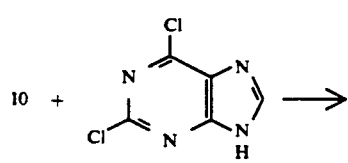 →

-continued

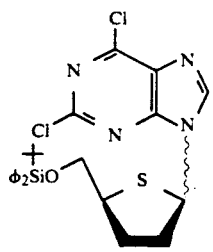
12

10 + 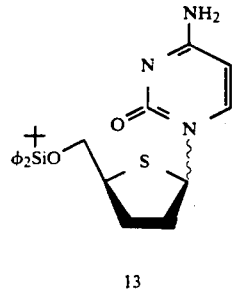 →

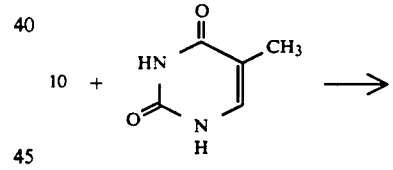
13

10 + 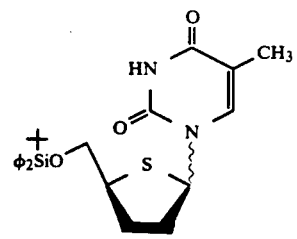 →

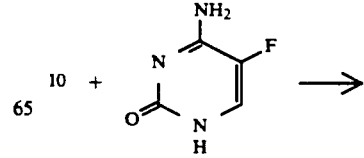
14

10 + (5-fluorocytosine) →

-continued
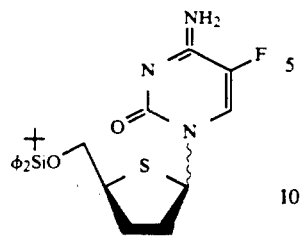
26
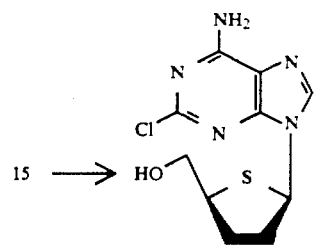
18
Compounds 11 through 14 and compound 26 can be further processed, for example, through deprotection, separation of anomers, and transformations of the purines to give intermediates 15 and 16 and compounds 17 through 25 and compound 27 as illustrated in the following reactions schemes and described in Examples 13–23 and 25.
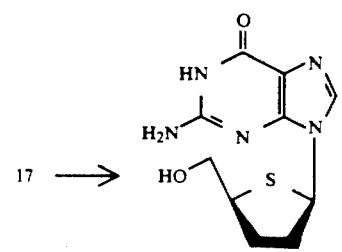
19
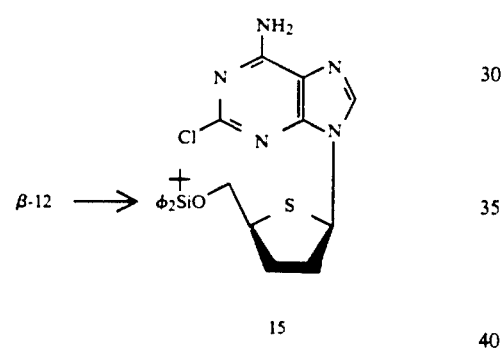
15
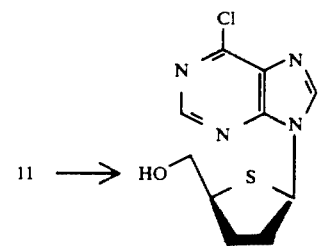
11 ⟶
20
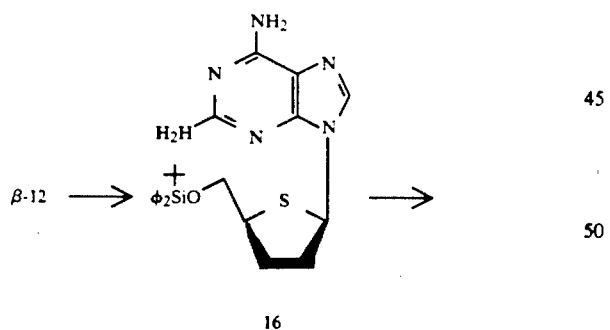
16
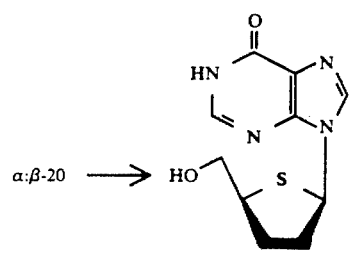
α:β-20 ⟶
21
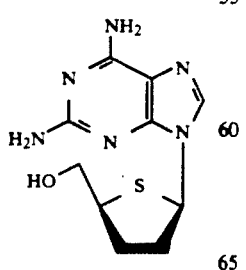
17
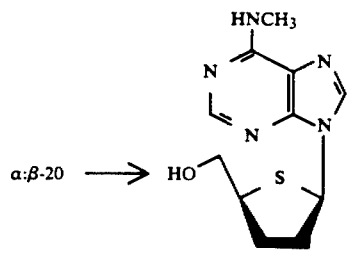
α:β-20 ⟶
22

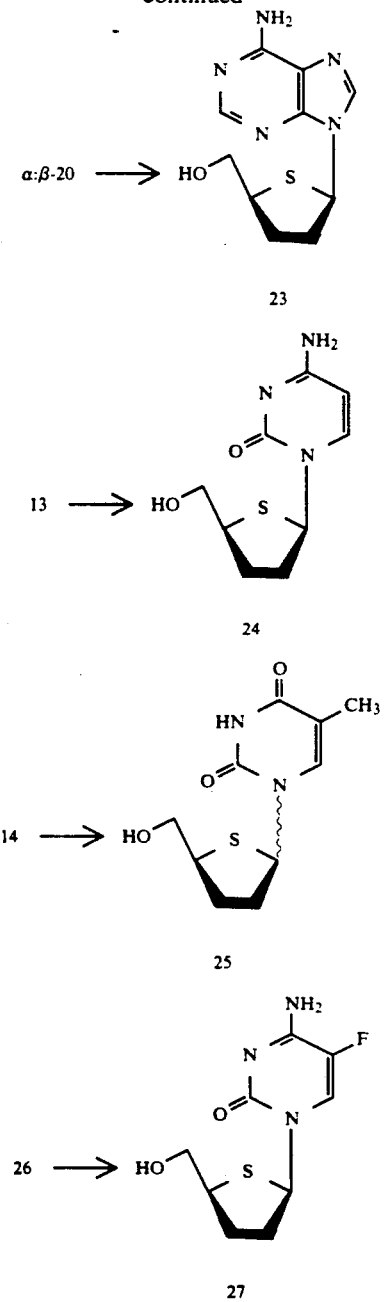

Known methods for altering 2',3'-dideoxyribonucleosides to produce 2',3'-dideoxy-3'-azidoribonucleosides and 2',3'-dideoxy-3'-fluoro-ribonucleosides may be used to convert 2',3'-dideoxy-4'-thio-ribonucleosides into 2',3'-dideoxy-3'-azido-4'-thio-ribonucleosides and 2',3'-dideoxy-3'-fluoro-4'-thio-ribonucleosides.

Compounds of the present invention are readily screened for anti-HIV activity by the following standard screening assay in CEM and MT2 cells.

1. Compound dilution and delivery to the plates. Test compounds are solubilized in the appropriate vehicle such as distilled water, DMSO, methyl alcohol, or other vehicle. The maximum solubility is determined as appropriate. Latex gloves, lab coats, and masks are used during all phases of the handling process to prevent exposure to potentially harmful agents. At highest solubility, the test compound is prepared and stored at $-20°$ C. until used by the screening laboratory. The first dilution of each compound is made tube with medium to yield a concentration two-fold that of the highest test concentration. Sterile titer tubes are then used to make serial one half log dilutions of each compound. Following dilution, the diluted compound is added to the appropriate well of a 96-well microtiter plate. Up to 12 dilutions can be conveniently assayed in triplicate on a single plate with all appropriate controls, including cell control, virus control, toxicity control, drug color control, medium control and plastic control. When testing includes only six dilutions, two drugs can be assayed on a single microtiter plate. The test compounds are added to the plate in a final volume of 100 microliters.

2. Cells and virus. During the time that the test compound dilutions are prepared, cells are washed and counted. Viability is monitored by trypan blue dye exclusion and assays are not performed if the viability falls below 90%. Cells are maintained in an exponential growth phase and are split 1:2 on the day prior to assay to assure adequate growth rate. For the primary screen, the cell line utilized is CEM cells. Experience has indicated that this cell line is able to detect all of the positive compounds detected on MT2 cells but is also able to detect activity with some compounds which are not detected with the MT2 cells. However, both cell lines are available and being used at all times and can be substituted or used in addition to CEM cells as requested. Unless otherwise indicated, the medium is phenol red-free RPMI 1640 with 10% heat-inactivated fetal calf serum (FBS), glutamine and antibiotics. Cells are propagated at $37°$ C. in an atmosphere of 5% $CO_2$ in air. The virus employed for this work is HIV-1 isolates IIIB and/or RF prepared by the acute infection process as follows: Briefly, virus infected cells are pelleted on a daily basis beginning at three days post-infection until the virus has killed all of the cells in the culture. Reverse transcriptase activity and p24 ELISA are used to identify pools with the greatest amount of virus. These 24-hour harvests are pooled, filtered and frozen at $-90°$ C. Prior to use in the assay the virus is titered on all available cells lines in order to determine the amount of virus required in the assay. In general, pools produced by the acute virus method require the addition of one microliter of infectious virus per well resulting in the screening of drugs on a multiplicity of infection of 0.01. In this manner enough virus is prepared and frozen to complete over one thousand microtiter plates, allowing the testing of up to two thousand compounds from a single stock. The use of a single stock of virus for a long period of testing has had very favorable effects on the repeatability of the assay systems. Virus infection of the CEM cells is carried in a bulk infection process. The appropriate number of cells required to complete the assay are mixed with infectious virus in a conical centrifuge tube in a small total volume of 1-2 milliliters. Following a one hour incubation the infected cells are brought to the appropriate final concentration of $5 \times 10$cells per milliliter with fresh tissue culture medium and 100 microliters are added to the appropriate experimental and virus control wells. Uninfected cells at the same concentration are plated for the toxicity controls and for the cell controls.

3. Evaluation of CPE-inhibition. Following the addition of cells and test compounds to the microtiter plate, the plate is incubated for 6 days at $37°$ C. Experience has determined that incubation for longer periods of time (7-8 days) or the use of higher input cell numbers (1×10⁴) results in between cell and virus controls.

The method of evaluating the antiviral assay involves the addition of 20 microliters of the tetrazolium salt MTT at 5 mg/ml to each well of the plate for 4-8 hours. After this incubation period, the cells are disrupted by the addition of 50 μL OF 20% SDS in 0.01N HCl. The metabolic activity of the viable cells results in a colored reaction product which is measured spectrophotometrically in a Molecular Devices Vmax plate reader at 570 nm. The optical density (O.D.) value is a function of the amount of formazan product, which is proportional to the number of viable cells. The plate reader is on-line to the screening laboratory microcomputer which evaluates and calculates plate data. The plate report provides a rundown of all pertinent information including the raw O.D. values, the calculated mean O.D.'s and the percent reduction in viral CPE as well as calculations including $TC_{50}$, $IC_{50}$ and antiviral and specificity indices. Finally, the results may include a plot which visually demonstrates the effect of the compound on uninfected cells (toxicity) and the protective or nonprotective effect of the compound on the infected cells.

The appropriate pharmaceutical carriers and diluents and the optimal dosages and regimens of the 2',3'-dideoxy-4'-thioribonucleosides as described herein for the treatment of humans infected with human immunodeficiency virus can be readily ascertained by those skilled in the art.

The following examples illustrate the preparation of the compounds of this invention. In these examples, the various compound numbers refer to the compounds shown in the foregoing reaction schemes. In these examples, DAST is diethylaminosulfur trifluoride, Dibal-H is diisobutylaluminum hydride, DMAP is 4-dimethylaminopyridine, HMDS is 1,1,1,3,3,3-hexamethyldisilazane, TMS-Cl is chlorotrimethylsilane, EtOAc is ethyl acetate, THF is tetrahydrofuran, LAH is lithium aluminum hydride, MeOH is methyl alcohol, EtOH is ethyl alcohol, DMF is dimethylformamide and TEAB is tetraethylammonium bromide.

EXAMPLE 1

1-(2-Deoxy-4-thio-5-O-trityl-β-D-ribofuranosyl)thymine (2)

A solution of 365 mg (1.42 mmol) of 1 in 20 mL of pyridine containing 486.5 mg (1.75 mmol) of triphenylmethyl chloride was heated at 100° C. with stirring for 0.5 hours. The cooled reaction mixture was poured in a thin stream into 1.5 L of vigorously stirred ice water. The product was collected, washed with generous quantities of H₂O, and dried. The off white solid was crystallized from acetone/benzene; yield 600 mg; mp. 120°-121° C.; MS FAB 501 (M+1)+; ¹H NMR (CDCl₃, 300 MHz) δ 1.42 (s, 3H, C-5, CH₃), 2.0 (m, 1, H-2'), 2.45 (m, 1, H-2'), 2.82 (brs, 1, 3'-OH), 3.22 (m, 1, CH₂), 3.64 (m, 2H, CH₂, H-4'), 4.50 (brs, 1, H-3'), 6.45 (t, 1, J=4 Hz, H-1'), 7.35 (m, 11H, aromatic and H-6), 7.45 (m, 5H, aromatic), 9.2 (s, 1, H-3).

EXAMPLE 2

2,3'-Anhydro-2'-deoxy-4'-thio-1-β-D-ribofuranosylthymine (3)

To a solution of 2 (300 mg) in 10 mL of CH₂Cl₂ was added 0.1 mL of DAST at −78° C. and the reaction mixture was slowly warmed to room temperature. The reaction mixture was poured into 100 mL of H₂O, extracted with 2×50 mL CH₂Cl₂, and evaporated to dryness to afford a pale yellow solid, 235 mg. MS FAB 483 (M+1)+; ¹H NMR (CDCl₃, 300 MHz) δ 1.9 (s, 3H, C-5, CH₃), 2.45 (m, 1H, H-2'), 2.95 (m, 1H, H-2'), 3.45 (m, 1H, CH₂), 3.70 (m, 2H, CH₂ and H-4'), 5.20 (brt, 1H, H-1'), 5.34 (brt, 1H, H-3'), 6.80 (s, 1H, H-6), 7.26 (m, 1OH, aromatic), 7.44 (m, 5H, aromatic).

EXAMPLE 3

2'-Deoxy-3'-azido-4'-thio-5'-O-trityl-β-D-ribofuranosylthymine (4)

To a solution of 3 (200 mg) in 20 mL of DMF was added sodium azide (100 mg) and the reaction mixture was heated at 120° C. for 24 hours, cooled to room temperature, poured into 100 mL of H₂O and extracted with CH₂Cl₂. Evaporation of solvent gave a syrup which after column chromatography afforded a white amorphous solid (125 mg); MS FAB 526 (M+1)+; ¹H NMR (CDCl₃, 300 MHz) δ 1.65 (s, 3H, C-5, CH₃), 2.05 (m, 1H, H-2'), 2.40 (m, 1, H-2'), 3.26 (m, 1, H-4'), 3.52 (m, 2, CH₂), 4.30 (m, 1, H-3'), 6.35 (t, 1, J=4 Hz, H-1'), 7.50 (m, 16, ArH, H-6), 8.72 (s, 1, H-3).

EXAMPLE 4

1-(2-Deoxy,3-azido-4-thio-β-D-ribofuranosyl)thymine (5)

A solution of 4 (50 mg) in 10 mL of 80% CH₃COOH was heated at 60° C. for 2 hours, cooled at room temperature and evaporated under reduced pressure to dryness to afford a solid which was purified on a thick preparative plate (CHCl₃/MeOH 85:15) to give 12 mg of −5; mp. 120°-121° C.; mp. 120°-121° C.; MS FAB 284 (M+H)+; ¹H NMR (DMSO-d₆, 300 MHz) δ 1.80 (s, 3, CH₃), 2.34 (m, 1, H-2'), 2.45 (m, 1, H-2'), 3.40 (m, 1, H-4'), 3.65 (m, 2, CH₂), 4.52 (m, 1, H-3'), 5.34 (t, 1, J=2.4 Hz, OH-5'), 6.16 (t, 1, J=4 Hz, H-1'), 7.84 (s, 1, H-6), 11.36 (s, 1, H-3).

EXAMPLE 5

5-t-Butyldiphenylsilyloxy-4-(S)-hydroxypentanoic acid, methyl ester (7)

To lactone 6 (5g, 14.1 mmol) dissolved in 250 mL of ethanol was added a solution of NaOH (564 mg, 14.1 mmol) in 14.5 mL water. The reaction mixture was stirred 1 hour, then the solvent was removed azeotropically with toluene. The residue was redissolved in 50 mL dimethylsulfoxide and 10 mL toluene and treated with dimethyl sulfate (1.6 mL, 17 mmol). After stirring 2 h at 25° C., the reaction was poured into 200 mL of ice water and extracted with 2×75 mL ethyl ether and 1×50 mL toluene. The organic phase was washed with 4×100 mL water and dried (MgSO₄). The solvent was removed in vacuo and the residue was filtered through a 40-g silica gel pad with 3:1 hexane/ethyl acetate. Solvent removal afforded 5.30 g (97%) of a viscous oil; FAB MS 329 (m-t-butyl)+; ¹H NMR (CCl₄) δ 7.8-7.2 (m, 10, ArH), 3.7 (m, 1, H-4), 3.65 (s, 3, OCH₃), 3.6 (m, 1, OH), 3.4 (m, 2, CH₂), 2.4 (m, 2, CH₂), 1.8 (m, 2, CH₂), 1.1 (s, 9, t-butyl).

EXAMPLE 6

5-t-Butyldiphenylsilyloxy-4-(R)-iodopentanoic acid, methyl ester (8)

To a solution of 7 (4.33 g, 11.2 mmol) in 250 mL toluene was added triphenylphosphine (5.9 g, 22.4 mmol), imidazole (2.3 g, 33.6 mmol), and iodine (4.26 g, 16.8 mmol) under a nitrogen atmosphere. The reaction mixture was lowered into a preheated heating mantle and refluxed for 1 hour. The reaction mixture was quenched by pouring into 200 mL saturated NaHCO$_3$ solution. Excess triphenylphosphine was destroyed by the addition of iodine until an iodine coloration remained in the organic phase. The organic phase was then washed with 5% sodium thiosulfate solution (2×100 mL) and 2×200 mL water. The product was purified by flash chromatography with 6:1 hexane/ethyl acetate yield 4.75 g (85%) of a viscous oil; $[\alpha]_D^{25}$+6.5° (C=1, CHCl$_3$); FAB MS 497 (M+H)$^+$, 439 (M-t-butyl)$^+$; $^1$H NMR (CDCl$_3$) δ 7.89 (m, 4, ArH), 7.4 (m, 6, ArH), 4.15 (m, 1, H-4), 3.85 (m, 2, CH ), 3.7 (s, 3, OCH$_3$), 2.5 (m, 2, CH$_2$), 2.25 (m, 1, H-2), 2.1 (m, 1, H-2), 1.1 (s, 9, t-butyl).

EXAMPLE 7

4-(S)-Acetylthio-5-t-butyldiphenylsilyloxypentanoic acid, methyl ester (9)

Thioacetic acid (1 mL, 13.2 mmol) was added to 20 mL of toluene under a nitrogen atmosphere. A 1 M solution of tetrabutylammonium hydroxide in methanol (11 mL, 11 mmol) with a washing of 1 mL methanol was added to the thioacetic acid solution. The methanol was removed azeotropically with toluene and residual salt redissolved in 30 mL toluene. The salt solution with a washing of 20 mL toluene was added to a solution of 8 (4.75 g, 9.6 mmol) in 50 mL toluene and stirred under nitrogen for 18 hours. After removal of solvent and precipitated salts, the crude product was purified by flash chromatography with 6:1 hexane/ethyl acetate. Yield 3.47 g (81%) of a viscous oil $[\alpha]_D^{25}$−16.0° (C=0.7, CDCl$_3$); FAB MS 445 (M+H)$^+$, 387 (M-t-butyl)$^+$; $^1$H NMR (CDCl$_3$) δ 7.65 (m, 4, ArH), 7.4 (m, 6, ArH), 3.8 (m, 1, H-4), 3.7 (s, 3, OCH$_3$), 3.7 (m, 2, CH$_2$), 2.35 (m, 2, CH$_2$), 2.3 (s, 3, acetyl CH$_3$), 2.2 (m, 1, H-2), 1.9 (m, 1, H-2), 1.05 (s, 9, t-butyl).

EXAMPLE 8

1-O-Acetyl-5-O-t-butyldiphenylsilyl-4-thio-2,3-dideoxyribofuranose (10)

A solution of 9 (1 g, 2.25 mmol) in 14 mL dry hexane and 2 mL toluene was cooled to −78° C. under nitrogen. A 1.5 M toluene solution of Dibal-H (3.0 mL, 4.5 mmol) was added over a 2 minute period with stirring continued for an addition 30 minutes. The reaction was quenched with 1.2 mL methanol and allowed to reach 25° C. Then 2.5 mL of saturated NaHCO$_3$ solution was added followed by 1.5 mL ethyl acetate. The mixture was dried with MgSO$_4$. The solids were removed by filtration and washed with ethyl acetate. After removal of solvent in vacuo the residue was redissolved in 20 mL dichloromethane and treated with DMAP (10 mg), pyridine (0.9 mL, 10 mmol) and acetic acid (0.47 mL, 5 mmol) with stirring under nitrogen overnight. The reaction mixture was shaken with 50 mL water, than 50 mL of 1% NaHCO$_3$. After drying (MgSO$_4$), the solvent was removed in vacuo and the residue purified by flash chromatography with 8:1 hexane/ethyl acetate: yield 0.78 g (83%) of a viscous oil; FAB MS 357 (M-t-butyl)$^+$; $^1$H NMR (CDCl$_3$) δ 7.68 (m, 4, ArH), 7.4 (m, 6, ArH), 6.0 (m, 1, ArH), 3.75 (m, 1, H-5), 3.5 (m, 1, H-4), 3.5 (m, 1, H-5), 2.15 (m, 2, CH$_2$), 2.0 (2s, 3, aromatic acetyls), 1.9 (m, 2, CH$_2$), 1.05 (s, 9, t-butyl).

EXAMPLE 9

9-(5-O-t-Butyldiphenylsilyl-4-thio-2,3-dideoxy-D-ribofuranosyl)-6-chloropurine (11)

A mixture of 10 (0.43 g, 1.04 mmol) and 6-chloropurine (0.24 g, 1.56 mmol) in 17 mL acetonitrile was cooled to 0° C. and a 1.8 M toluene solution of diethylaluminum chloride (0.59 mL, 1.06 mmol) was added over 1 minute. Stirring was continued at 0° C. for 5 minutes and at 25° C. for 10 minutes. The reaction mixture was quenched by pouring into a mixture of 20 mL dichloromethane and 10 mL saturated NaHCO$_3$. The organic phase was dried (MgSO$_4$) and concentrated in vacuo. The residue was flash chromatographed with 9:1 hexane/ethyl acetate followed by 4:1 hexane/ethyl acetate. Solvent removal gave a 1:1 α/β anomeric mixture: yield 0.315 g (59%); FAB MS 509 (M+H)$^+$; $^1$H NMR (CDCl$_3$) of β anomer, δ 8.7 (s, 1, H-2), 8.45 (s, 1, H-8), 7.7 (m, 4, ArH), 7.4 (m, 6, ArH), 6.27 (m, 1, 7'-H), 3.95 (m, 1, 5'-H), 3.85 (m, 2, 4'-H, 5'-H), 2.45 (m, 2, 2'-H's), 2.25 (m, 1, 3'-H), 1.85 (m, 1, 3'-H), 1.1 (s, 9, t-butyl).

EXAMPLE 10

9-(5-O-t-Butyldiphenylsilyl-4-thio-2,3-dideoxy-D-ribofuranosyl)-2,6-dichloropurine (12)

A mixture of 10 (0.25 g, 0.6 mmol), 2,6-dichloropurine (0.142 g, 0.75 mmol) in 10 mL acetonitrile was cooled to 0° C. and a 1.8 M toluene solution of diethyl aluminum chloride (0.345 mL, 0.62 mmol) was added over 1 min. Stirring was continued at 0° C. for 5 minutes and at 25° C. for 10 minutes. The reaction mixture was quenched by pouring into a mixture of 20 mL dichloromethane and 10 mL saturated NaHCO$_3$. The organic phase was dried (MgSO$_4$) and concentrated in vacuo. The residue was flash chromatographed with 15:1 toluene/ethyl acetate. Solvent removal gave 98 mg (30%) of 12. FAB MS 543 (M+H)$^+$; $^1$H NMR (CDCl$_3$) δ 8.47 (s, 1, H-8), 7.7 (m, 4, ArH), 7.45 (m, 6, ArH), 6.22 (m, 1, 1'-H), 3.96 (m, 1, 5'-H), 3.85 (m, 2, 4'-H, 5'-H), 2.45 (m, 2, 2'-H's), 2.25 (m, 1, 3'-H), 1.82 (m, 1, 3'-H), 1.1 (s, 9, t-butyl).

EXAMPLE 11

5'-O-t-Butyldiphenylsilyl-4'-thio-2',3'-dideoxycytidine (13)

A mixture of 10 (0.26 g, 0.63 mmol), cytosine (0.105 g, 0.95 mmol), and potassium nonafluorobutanesulfonate (0.77 g, 2.3 mmol) was suspended in 12 mL dry acetonitrile under nitrogen. HMDS (0.135 mL, 0.63 mmol) and TMS-Cl (0.37 mL, 2.9 mmol) were added sequentially via syringe and the reaction stirred at 25° C. overnight. The reaction was poured into a mixture of 20 mL dichloromethane and 15 mL saturated NaHCO$_3$ and shaken. The organic phase was dried (MgSO$_4$) and concentrated in vacuo. The anomeric mixture was separated by preparative TLC with 7.5% MeOH/CHCl$_3$ with an ammonia atmosphere: yield of β-anomer, 78 mg and 117 mg of the α-anomer to afford total yield of 195 mg (66.5%); FAB MS 466 (M+H)$^+$; $^1$H NMR (CDCl$_3$) of α/β anomer, δ 8.12 (d, 1, 6-H), 7.7 (m, 4, ArH), 7.4 (m, 6, ArH), 6.32 (m, 1, 1'-H), 5.9–5.3 (hump, 1, NH$_2$), 5.75 (d, 1, 5-H), 5.45 (d, 1, 5-H), 3.75 (m, 3, 4'-H$_{\alpha,\beta}$'s, 3'-H$_{\alpha,\beta}$'s).

EXAMPLE 12

5'-O-t-Butyldiphenylsilyl-4'-thio-3'-deoxythymidine (14)

Using the procedure for Example 11, 4'-thioribose 10 (0.35 g, 0.83 mmol), thymine (0.13 g, 1.05 mmol), potassium nonafluorobutanesulfonate (0.875 g, 2.54 mmol), HMDS (0.175 mL, 0.83 mmol), and TMS-Cl (0.4 mL, 3.2 mmol), following purification by preparative TLC (8:1 dichloromethane/acetonitrile) afforded 371 mg (92.5%) of 14, as a 4:3 $\alpha$:$\beta$ anomeric mixture; FAB MS 481 (M+H)+; $^1$H NMR (CDCl$_3$) $\delta$ 9.65 (s, 1, NH), 7.7 (m, 4, ArH), 7.4 (m, 6, ArH), 6.3 (m, 1, 1'-H$_{\alpha,\beta}$), 3.88 (m, 1, 4'-H$_\alpha$), 3.82 (d, 1, 5'-H$_\beta$), 3.66 (d+m, 2, 4'-H$_\beta$, 5'-H$_\alpha$), 2.4–1.85 (m, 4, 2'-H$_{\alpha,\beta}$'s, 3'-H$_{\alpha,\beta}$'s), 1.95 (s, 3, 5$_\beta$-CH$_3$), 1.77 (s, 3, 5$_\beta$-CH$_3$), 1.11 (s, 9, $\beta$-t-butyl), 1.07 (s, 9, $\alpha$-t-butyl).

EXAMPLE 13

9-(5-O-t-Butyldiphenylsilyl-4-thio-2,3-dideoxy-D-ribofuranosyl)-2-chloro-6-aminopurine (15)

A mixture of 12 (150 mg) and saturated ethanolic ammonia (50 mL) was heated at 50° C. in a glass-lined stainless steel pressure vessel for 48 hours. The reaction mixture was evaporated to dryness to afford a syrup which was purified on two silica gel thick plates (Analtech, GF, 1000 $\mu$m) that were developed in 99:1 CHCl$_3$-MeOH. The product was eluted with CHCl$_3$ and evaporated. The residue was crystallized from EtOAc-cyclohexane to give pure 15 (125 mg, 86%); mp. 123°–125° C.; FAB MS 524 (M+H)+; $^1$H NMR (CDCl$_3$) $\delta$ 8.14 (s, 1, H-8), 7.72 (m, 4, ArH), 7.42 (m, 6, ArH), 6.02 (brs, 2, NH$_2$), 6.16 (m, 1'-H), 3.93 (m, 1, 5'-H), 3.84 (m, 1, 5'-H), 3.73 (m, 1, 4'-H), 2.36 (m, 2, 2'-H), 2.18 (m, 1, 3'-H), 1.90 (m, 1, 3'-H), 1.1 (s, 9, t-butyl).

EXAMPLE 14

9-(5-O-t-Butyldiphenylsilyl-4-thio-2,3-dideoxy-D-ribofuranosyl)-2,6-diaminopurine (16)

A solution of 12 (117.5 mg, 0.22 mmol) and lithium azide (54 mg, 1.1 mmol) in 10 mL 95% ethanol was refluxed for 2 hours. The solvent was removed in vacuo and the residue was partitioned between dichloromethane and water. The organic phase was dried (MgSO$_4$) and concentrated in vacuo to a residue which was redissolved in 15 mL ethyl ether. The etheral solution was then treated with LAH (0.1 g, 2.6 mmol) for 0.5 h at 25° C. The excess LAH was decomposed by the addition of 20% water/THF followed by the addition of Celite and filtration. The residue was washed with ethyl/ether and the filtrates were concentrated to give the crude diamino compound. The product was purified by preparative TLC with 95:5 chloroform/methanol to afford 90 mg (80%) of 16. FAB MS 505 (M+H)+; $^1$H NMR (CDCl$_3$) $\delta$ 7.83 (s, 1, H-8), 7.68 (m, 4, ArH), 7.42 (m, 6, ArH), 6.02 (m, 1, 1'-H), 5.4 (brs, 2, NH$_2$), 4.68 (brs, 2, NH$_2$), 3.93 (m, 1, 5'-H), 3.83 (m, 1, 5'-H), 3.72 (m, 1, 4'-H), 2.35 (m, 2, 2'-H's), 2.17 (m, 1, 3'-H), 1.88 (m, 1, 3'-H), 1.8 (brs, CH$_3$OH), 1.43 (s, CH$_3$OH), 1.1 (s, 9, t-butyl).

EXAMPLE 15

9-(4-Thio-2,3-dideoxy-D-ribofuranosyl)-2,6diaminopurine (17)

A mixture of 16 (50 mg, 0.1 mmol), acetic acid (7 $\mu$L, 0.12 mmol), and 0.17 mL of 1 M tetrabutylammonium fluoride in THF (0.17 mmol) was stirred in 10 mL tetrahydrofuran overnight. Water (2 mL) and 15 mL ethyl ether were added followed by stirring for 5 minutes. The organic phase was extracted with 2 mL water and then the combined aqueous solution was washed with 15 mL ethyl ether. The aqueous extract was concentrated in vacuo to 1 mL and then applied to a 4-mL Dowex 1×4 100–200 ($^-$OH) column to remove tetrabutylammonium salts by eluting with water followed by 20% aqueous methanol. The solvent was removed in vacuo and the product was recrystallized from ethanol/ethyl acetate to afford 19.5 mg (54%) of 17; mp. 187°–90° C. dec; FAB MS 267 (M+H)+; $^1$H NMR (DMSO-d$_6$) $\delta$ 8.0 (s, 1, H-8), 6.68 (br, s, 2, NH$_2$), 5.95 (m, 1, 1'-H), 5.71 (brs, 2, NH$_2$), 5.22 (m, 1, 5'-OH), 3.73 (m, 1, 5'-H), 3.57 (m, 2, 4'-H, 5'-H), 2.4 (m, 1, 2'-H), 2.32 (m, 1, 2'-H), 2.12 (m, 1, 3'-H), 1.98 (m, 1, 3'-H).

EXAMPLE 16

9-(4-Thio-2,3-dideoxy-D-ribofuranosyl)-2-chloro-6aminopurine (18)

To a solution of 15 (100 mg, 0.19 mmol) in 5 mL of THF was added CH$_3$COOH (14 $\mu$L, 0.24 mmol) and 1 M solution of tetrabutylammonium fluoride in MeOH (0.4 mL, 0.4 mmol) followed by stirring for 1 hour. One drop of pyridine was added and then solvent was evaporated in vacuo. The residue was purified by preparative TLC using 90:10 CHCl$_3$-MeOH as eluant to afford crude 18 which was crystallized by EtOH to give pure 18 (38 mg, 70%); mp. 125°–127° C.; FAB MS 286 (M+H)+; $^1$H NMR (DMSO-d$_6$) $\delta$ 8.45 (s, 1, H-2), 7.80 (brs, 2, NH$_2$), 6.10 (m, 1, 1'-H), 5.12 (m, 1, 5'-OH), 3.75 (m, 1, 4'-H), 3.61 (m, 2, 5'-H), 2.40 (m, 2, 2'-H), 2.15 (m, 1, 3'-H), 2.0 (m, 1, 3'-H).

EXAMPLE 17

4'-Thio-2',3'-dideoxy-guanosine (19).

To a solution of 17 (50 mg, 0.18 mmol) in 20 mL of a 0.75 M TEAB buffer was added 6 $\mu$L of adenosine deaminase. The reaction was stirred for 12 days followed by lyophilization. The residue was purified by preparative TLC with 4:1 CHCl$_3$-MeOH. The crude product was recrystallized from hot EtOH to give 19 (40 mg, 80%); mp. 180°–183° C., FAB MS 268 (M+H)+; $^1$H NMR (DMSO-d$_6$) $\delta$ 10.8 (br, 1, NH), 8.0 (s, 1, H-8), 6.6 (s, 2, NH$_2$), 5.90 (m, 1, 1'-H), 5.12 (brs, 1, 5'-OH), 3.72 (m, 1, 4'-H), 3.55 (m, 2, 5'-H), 2.35 (m, 2, 2'-H), 2.15 (m, 1, 3'-H), 1.95 (m, 1, 3'-H).

EXAMPLE 18

9-(4-Thio-2,3-dideoxy-D-ribofuranosyl)-6-chloropurine (20)

A solution of 11 (0.315 g, 0.62 mmol), acetic acid (30 $\mu$L, 0.63 mmol) and tetrabutylammonium fluoride (1 M in THF, 0.65 mL, 0.65 mmol) in 3 mL THF was stirred for 10 minutes under nitrogen. The solvent was removed in vacuo and the residue flash chromatographed with dichloromethane followed by 19:1 chloroform/methanol to give 0.164 g (98%) of the anomers. The anomers were separated by centrifugal chromatography with 19:1 chloroform/methanol: yield of $\beta$-anomer 10 mg; mp. 125°–128° C.; [$\alpha$]$_D^{25}$+2.5° (c=0.1 CH$_3$OH); FAB MS 271 (M+H)+; $^1$H NMR (CDCl$_3$) $\delta$ 9.0 (s, 1, H-2), 8.8 (s, 1, H-8), 6.3 (m, 1, 5'-OH), 3.8 (m, 1, 5'-H), 3.65 (m, 2, 4'-H, 5'-H), 2.6 (m, 1, 2'-H), 2.45 (m, 1, 2'-H), 2.2 (m, 1, 3'-H), 2.0 (m, 1, 3'-H).

EXAMPLE 19

4'-Thio-2',3'-dideoxyinosine (21)

To a solution of the α/β anomers of 20 (82 mg, 0.3 mmol) in 20 mL of a 0.75 M TEAB buffer was added 3 μL adenosine deaminase. The reaction was stirred 34 h followed by lyophilization. The residue was purified by preparative TLC with 6:1 chloroform-methanol containing 1% acetic acid. The crude product was recrystallized from methanol/carbontetrachloride to give 30.5 mg (79%) of 21; mp. 195°–197° C.; $[\alpha]_D^{25}$ −13.9° (c=0.1, H$_2$O); FAB MS 253 (M+H)+; $^1$H NMR (D$_2$O) δ 8.5 (s, 1, H-2), 8.2 (s, 1, H-8), 6.2 (m, 1, 1'-H), 3.95 (m, 1, 5'-H), 3.8 (m, 2, 4'-H, 5'-H), 2.5 (m, 2, 2'-H's), 2.3 (m, 1, 3'-H), 1.9 (m, 1, 3'-H).

EXAMPLE 20

N$^6$-Methyl-4'-thio-2',3'-dideoxyadenosine (22)

The anomeric mixture of 20 (0.132 g, 0.49 mmol) in a steel bomb was stirred with 20 mL 40% methylamine in water at 80° C. overnight. After solvent removal in vacuo, the residue was purified by preparative TLC with 9:1 chloroform/methanol to give 100 mg (77%) of the anomeric mixture. The anomers were partially separated by a Dowex 1×4 (-OH) column with 10% aqueous methanol to give 37 mg of impure β anomer which was recrystallized from hexane-ethyl acetate to afford 22.5 mg of pure β anomer by HPLC; mp. 131°–134° C.; FAB MS 266 (M+H)+; $^1$H NMR (DMSO-d$_6$) δ 8.4 (s, 1, H-2), 8.2 (s, 1, H-8), 7.7 (brs, 1, NH), 6.2 (m, 1, 1'-H), 5.15 (m, 1, 5'-OH), 3.75 (m, 1, 5'-H), 3.6 (m, 2, 4'-H, 5'-H), 2.95 (s, 3, CH$_3$), 2.4 (m, 2, 4'-H's), 2.15 (m, 1, 3'-H), 2.0 (m, 1, 3'-H).

EXAMPLE 21

4'-Thio-2',3'-dideoxyadenosine (23)

A mixture of α/β anomer 20 (80 mg, 0.3 mmol) and 50 mL of saturated ammonia/methanol was heated at 80° C. for three days. The solvent was removed in vacuo and the residue purified by preparative TLC with 9:1 chloroform/methanol to give 55 mg (73%) of the adenosine anomers. The anomeric mixture was separated by ion exchange chromatography (elution with water) to give after recrystallization from ethanol/ethyl acetate 7.5 mg of predominantly β-anomer; mp. 179°–182° C.; $^1$H NMR (DMSO-d$_6$) δ 8.4 (s, 1, H-2), 8.15 (s, 1, H-8), 7.25 (s, 2, NH$_2$), 6.15 (m, a, 1'-H), 5.15 (brs, 1, 5'-OH), 3.75 (m, 1, 5'-H), 3.6 (m, 2, 4'-H, 5'-H), 2.4 (m, 2, 2'-H's), 2.15 (m, 1, 3'-H), 2.0 (m, 1, 3'-H).

EXAMPLE 22

4'-Thio-2',3'-dideoxycytidine (24)

The compound 13 (78 mg, 0.17 mmol) was dissolved in 4 mL tetrahydrofuran and then 1 M tetrabutylammonium fluoride in THF (0.2 mL, 0.2 mmol) and acetic acid (11.5 μm, 0.2 mmol) were added, with subsequent stirring at 25° C. overnight. The reaction was diluted with 10 mL water and 10 mL ethyl ether followed by stirring for 5 minutes. The aqueous phase was washed with 20 mL ethyl ether and concentrated in vacuo to 1 mL. The aqueous residue was eluted through a 5-mL Dowex 1×4 (-OH) column with water to remove the tetrabutyl ammonium salts. The crude product (33 mg, 87%) was refractory to recrystallization and was precipitated as an amorphous solid with ethyl acetate and ethyl ether to afford 26.5 mg (69%) of 24; mp. 83°–85° C.; FAB MS 228 (M+H)+;$^1$H NMR (DMSO-d$_6$) δ 8.0 (d, 1, H-6), 7.1 (brd, 2, NH$_2$), 6.15 (m, 1, 1'-H), 5.74 (d, 1, H-5), 5.1 (brs, 1, 5'-OH), 4.2 (q, EtOAc), 3.64 (m, 1, 5'-H), 3.5 (m, 2, 4'-H, 5'-H), 2.18 (m, 1, 2'-H), 2.0 (m, 2, 2'-H, 3'-H), 1.99 (s, EtOAc), 1.82 (m, 1, 3'-H), 1.18 (t, EtOAc).

EXAMPLE 23

4'-Thio-3'-deoxythymidine (25)

To a solution of 14 (0.136 g, 0.28 mmol) in 3 mL tetrahydrofuran was added acetic acid (17 μL, 0.3 mmol) and 0.3 mL (0.3 mmol) 1 M tetrabutylammonium fluoride in THF, followed by stirring for 1 hour. One drop of triethylamine was added and then solvent was removed in vacuo. The residue was flashed chromatographed with dichloromethane followed by 95:5 chloroform/methanol to afford a quantitative yield of the anomeric mixture. Attempted separation of the anomers by ion exchange chromatography (elution with water) gave fraction 1 (1:3 α/β), fraction 2 (1:1 α/β), and fraction 3 (4:1 α/β). Crystallization of fraction 1 from ethyl acetate/hexane gave 3.9 mg of 25 (2:3 α/β); in similar fashion fraction 2 gave 18.6 mg of 25 (7:3 α/β). Recrystallization of the fraction 2 mother liquors gave an additional 8.8 mg of 25 (1:1 α/β); mp. 138°–140° C.; FAB MS 243 (M+H)+; $^1$H NMR (DMSO-d$_6$) δ 11.3 (brs, 1, NH), 7.88, 7.73 (2s, 1, H$_{\alpha}$-6, H$_{\beta}$-6), 6.15 (m, 1, 1'-H$_{\alpha,\beta}$), 5.15, 5.0 (2m, 1, 5'-OH$_{\alpha,\beta}$), 3.73 (m, 0.5, 4'-H$_{\beta}$), 3.68 (m, 0.5, 5'-H$_{\beta}$), 3.62−3.42 (m, 1.5, 4'-H$_{\alpha}$, 5'-H$_{\alpha}$, 5'-H$_{\beta}$), 3.56 (m, 0.5, 5'-H$_{\alpha}$), 2.3 (m, 0.5, 2'-H$_{\beta}$), 2.24−2.04 (m, 2.5, 2'-H$_{\alpha,\beta}$3'-H$_{\alpha,\beta}$), 2.04−1.8 (m, 1, 3'-H$_{\alpha,\beta}$), 1.8 (2s, 3, 5$_{\alpha,\beta}$-CH$_3$).

EXAMPLE 24

5'-O-t-Butyldiphenylsilyl-4'-thio-2'3'-dideoxy-5-fluorocytidine (26)

A mixture of 10 (0.35 g, 0.84 mmol), 5-fluorocytosine (0.17 g, 1.32 mmol), and potassium nonafluorobutanesulfonate (1.05 g, 3.11 mmol) was suspended in 19 mL dry acetonitrile under argon. HMDS (0.20 mL, 0.95 mmol) and TMS-Cl (0.51 mL, 4.02 mmol) were added sequentially via syringe and the mixture was stirred at 25° C. for 24 hours. The reaction mixture was poured into a mixture of 50 mL dichloromethane and 30 mL saturated NaHCO$_3$ and stirred for 2 hours. The layers were separated, the aqueous layer was extracted twice with 50 mL dichloromethane and the combined extracts were dried (Na$_2$SO$_4$) and the solvent removed under reduced pressure to yield 0.385 g of residue. The crude product was purified by preparative TLC with 10% MeOH/CHCl$_3$ to afford 0.227 g (55.6%) of a 2:3 mixture of α- and β- anomers; FAB MS 484 (M+H)+; $^1$H NMR (CDCl$_3$) δ 8.09 (d, 0.4, 6-H, J$_{6,5-F}$=6.5 Hz), 7.99 (d, 0.6, 6-H, J$_{6,5}$-F=6.5 Hz), 7.71−7.64 (m, 4, ArH), 7.45−7.36 (m, 6, ArH), 6.24 (M, 1, 1'-H), 6.00−5.00 (br hump, NH$_2$), 3.90−3.62 (m, 3,4'-H and 5'-H), 2.39−2.23 (m, 1, 2'-H), 2.13−1.65 (m, 3, 2'- and 3'-H), 1.09 (s, 3.6, CH$_3$), 1.07 (s, 5.4, CH$_3$).

EXAMPLE 25

4'-Thio-2',3'-dideoxy-5-fluorocytidine (27)

Using the procedure of Example 22, compound 26 is dissolved in THF and treated with acetic acid and 1M tetrabutylammonium in THF to give compound 27.

EXAMPLE 26

Using the procedure of Example 11, compound 10 is reacted with one of the following pyrimidine bases to give the corresponding 5'-O-t-butyldiphenylsilyl-protected 4'-thio-2',3'-dideoxyribonucleoside: 5-ethyl cytosine; 5-fluoro cytosine; 5-bromo cytosine; 5-iodo cytosine; 5-chloro cytosine; 5-trifluoromethyl cytosine; 5-methyl cytosine; uracil; 5-fluoro uracil; 5-bromo uracil; 5-iodo uracil; 5-chloro uracil; 5-trifluoromethyl uracil; and 5-ethyl uracil.

EXAMPLE 27

Using the procedure of Example 22, a compound made according to Example 26 is deprotected to give the corresponding 4'-thio-2',3'-dideoxyribonucleoside.

EXAMPLE 28

Anti-HIV activity of 2', 3'-dideoxy-4'thioribonucleosides

Representative compounds according to present invention were tested for anti-HIV activity in MT-2 and CEM cells infected with HIV virus. The results were compared with that of two known anti-HIV agents, AZT and DDC. The results are summarized in Table I below.

TABLE I

| COMPOUND | CELL LINE | $IC_{50}$ ($\mu$g/mL) | $TC_{25}$ ($\mu$g/mL) | SI | TAI |
|---|---|---|---|---|---|
| 9-(4-thio-2,3-dideoxy-$\beta$-D-ribofuranosyl)-6-chloropurine | MT-2 | — | 21 | — | 0.0 |
| 4'-thio-2',3'-dideoxyinosine | MT-2 | — | >100 | — | >4.0 |
| 4'-thio-2'3'-dideoxyadenosine | MT-2 | 80 | >100 | 1.3 | >17 |
| $N^6$-methyl-4'-thio-2',3'-dideoxyadenosine | MT-2 | — | >100 | — | 1.0 |
| 9-(4-thio-2,3-dideoxy-$\beta$-D-ribufuranosyl)-2-chloro-6-aminopurine | CEM | — | 5.74 | — | — |
| 4'-thio-2',3'-dideoxycytidine | CEM | 1.0 | >100 | >100 | >65 |
| 9-(4-thio-2,3-dideoxy-$\beta$-D-ribofuranosyl)-2,6-diaminopurine | CEM | 37.0 | 97.0 | 2.6 | 21.0 |
| 4'-thio-2',3'-dideoxy-guanosine | CEM | — | >100 | — | 0.0 |
| 4'-thio-2',3'-dideoxy-guanosine | MT-2 | 98 | >200 | 1.6 | 11.0 |
| 4'-thio-3'-deoxythymidine | MT-2 | — | >100 | — | >4.0 |
| 4'-thio-3'-deoxythymidine | CEM | — | >150 | — | 4.0 |
| 1-(2-deoxy-3-azido-4-thio-$\beta$-D-ribofuranosyl)thymine | CEM | 0.45 | >100 | >222.02 | >60.15 |
| AZT | MT-2 | 0.14 | 9.3 | >160 | >82 |
|  | CEM | <0.03 | >10 | >313 | >93 |
| DDC | MT-2 | 0.44 | >9.8 | >25 | >52 |
|  | CEM | 0.05 | 5.3 | 120 | >63 |

All data represents the means of several experiments. $IC_{50}$ represents the minimum drug concentration ($\mu$g/mL) that inhibited CPE (cytopathogenic effects) by 50%, calculated by using a regression analysis program for semilog curve fitting. $TC_{25}$ represents the minimum drug concentration ($\mu$g/ml) that reduced cell viability by 25%. SI (selectivity index) is calculated by dividing the $TC_{25}$ by the $ID_{50}$. TAI (total antiviral index) is that area between the cytotoxicity and the antiviral curves.

Although the invention has been described in considerable detail with specific reference to certain advantageous embodiments thereof, variations and modifications can be made without departing from the scope of the invention as described in the specification and defined in the appended claims.

What is claimed is:

1. A compound represented by the formula

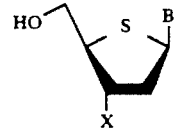

where
X=H, $N_3$ or F
and B is a member selected from the group consisting of pyrimidine, 5-azapyrimidine, 6-azapyrimidine, 3-deazapyrimidine, purine, 3-deazapurine, 7-deazapurine, 8-azapurine, and 2-azapurine bases.

2. A compound represented by the formula

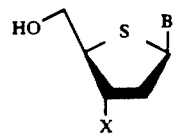

where
X=H, $N_3$ or F
and B is a member selected from the group consisting of the following pyrimidine and purine bases: uracil; thymine; cytosine; 5-ethyl cytosine; 5-methyl cytosine; 5-fluoro cytosine; 5-bromo cytosine; 5-iodo cytosine; 5-chloro cytosine; 5-trifluoromethyl cytosine; 5-fluoro uracil; 5-bromo uracil; 5-iodo uracil; 5-chloro uracil; 5-trifluoromethyl uracil; 5-ethyl uracil; adenine; guanine; hypoxanthine; 2-aminopurine; 2,6-diaminopurine; 2-chloro-6-aminopurine; 6-chloropurine; and $N^6$-methyladenine.

3. 1-(2-Deoxy-3-azido-4-thio-$\beta$-D-ribofuranosyl)thymine.

4. 9-(4-Thio-2,3-dideoxy-D-ribofuranosyl)-2,6diaminopurine.

5. 4'-Thio-2',3'-dideoxy-guanosine.

6. 4'-Thio-2',3'-dideoxyadenosine.

7. 4'-Thio-2',3'-dideoxycytidine.

8. 4'-Thio-2',3'-dideoxy-5-fluorocytidine.

UNITED STATES PATENT AND TRADEMARK OFFICE
CERTIFICATE OF CORRECTION

PATENT NO. : 5,128,458

DATED : July 7, 1992

INVENTOR(S) : John A. Montgomery and John A. Secrist, III

It is certified that error appears in the above-identified patent and that said Letters Patent is hereby corrected as shown below:

In column 1, between lines 9 and 11, insert the following:

-- This invention was made with Government support under Grant No. P01-CA-34200, awarded by the Department of Health and Human Services. The Government has certain rights in the invention. --

Signed and Sealed this

Fourteenth Day of September, 1993

*Attest:*

BRUCE LEHMAN

*Attesting Officer*     *Commissioner of Patents and Trademarks*